US008664160B2

(12) United States Patent
Ypema et al.

(10) Patent No.: US 8,664,160 B2
(45) Date of Patent: Mar. 4, 2014

(54) FUNGICIDAL MIXTURES

(75) Inventors: Hendrik Ypema, Cary, NC (US);
Andreas Hopf, Neustadt (DE); Nathan Froese, Winkler (CA); Reinhard Stierl, Kaohsiung County (TW)

(73) Assignee: BASF SE, Ludwigshafen (DE)

( * ) Notice: Subject to any disclaimer, the term of this patent is extended or adjusted under 35 U.S.C. 154(b) by 1100 days.

(21) Appl. No.: 12/092,658

(22) PCT Filed: Nov. 6, 2006

(86) PCT No.: PCT/EP2006/068098
§ 371 (c)(1),
(2), (4) Date: May 5, 2008

(87) PCT Pub. No.: WO2007/054469
PCT Pub. Date: May 18, 2007

(65) Prior Publication Data
US 2008/0293568 A1     Nov. 27, 2008

Related U.S. Application Data

(60) Provisional application No. 60/735,194, filed on Nov. 10, 2005.

(51) Int. Cl.
*A01N 43/653*    (2006.01)
*A01N 25/34*     (2006.01)
*A01P 3/00*      (2006.01)

(52) U.S. Cl.
USPC .......................................... 504/100; 514/183

(58) Field of Classification Search
None
See application file for complete search history.

(56) References Cited

U.S. PATENT DOCUMENTS

| 5,256,683 | A | 10/1993 | Hutt et al. |
| 5,380,743 | A | 1/1995 | Hutt et al. |
| 5,639,918 | A | 6/1997 | Hutt et al. |
| 5,869,517 | A | 2/1999 | Muller et al. |
| 6,054,592 | A | 4/2000 | Muller et al. |
| 6,365,614 | B1 | 4/2002 | Schelberger |
| 6,369,090 | B1 | 4/2002 | Schelberger et al. |
| 2005/0032903 | A1 | 2/2005 | Suarez-Cervieri et al. |

(Continued)

FOREIGN PATENT DOCUMENTS

| AU | 637779 | 7/1990 |
| AU | 685299 | 1/1996 |

(Continued)

OTHER PUBLICATIONS

'Benalaxyl-Mdatasheet' (www.alanwood.net/pesticides/benalaxyl-m.html).*

(Continued)

*Primary Examiner* — Dennis Heyer
(74) *Attorney, Agent, or Firm* — Brinks Gilson & Lione

(57) ABSTRACT

Fungicidal mixtures, comprising (1) triticonazole of the formula I or salts or adducts thereof and (2) pyraclostrobin of the formula II and (3) at least one acylalanine selected from the group consisting of metalaxyl-M of the formula III and (4) kiralaxyl of the formula IV in a synergistically effective amount, methods for controlling harmful fungi using mixtures of the compounds I to III or I, II and IV and the use of the compounds I to III or I, II and IV for preparing such mixtures, and also compositions comprising such mixtures.

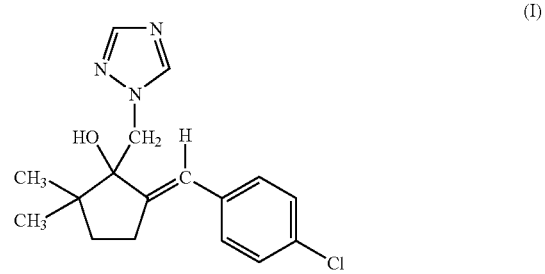

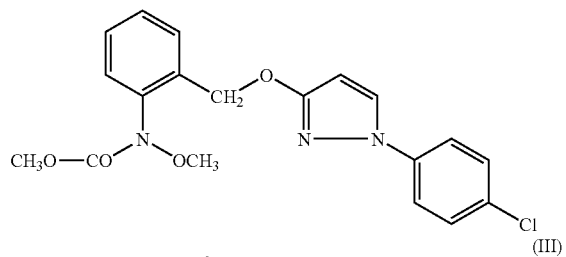

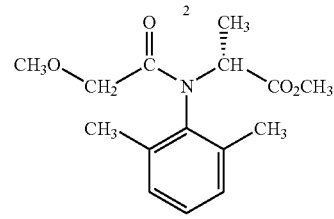

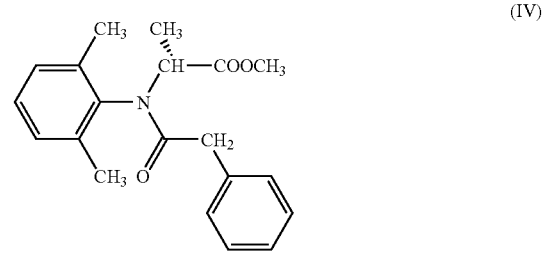

10 Claims, No Drawings

(56) References Cited

U.S. PATENT DOCUMENTS

| | | | |
|---|---|---|---|
| 2007/0155706 A1* | 7/2007 | Andersch et al. | 514/114 |
| 2008/0064601 A1 | 3/2008 | Casanello et al. | |
| 2008/0293707 A1 | 11/2008 | Gewehr et al. | |
| 2009/0096527 A1 | 4/2009 | Ishiguro | |
| 2009/0291994 A1 | 11/2009 | Ypema et al. | |

FOREIGN PATENT DOCUMENTS

| | | | | |
|---|---|---|---|---|
| CA | 2 568 817 | | 12/2005 | |
| EP | 0 378 953 A1 | | 12/1989 | |
| EP | 0 378 953 | | 7/1990 | |
| WO | WO 96/01256 | | 1/1996 | |
| WO | WO-96/01256 A1 | | 1/1996 | |
| WO | WO-96/01559 A1 | | 1/1996 | |
| WO | WO-98/54696 | | 12/1998 | |
| WO | WO 98/54969 | | 12/1998 | |
| WO | WO-98/54969 A1 | | 12/1998 | |
| WO | WO-98/58544 | | 12/1998 | |
| WO | WO 98/58544 | | 12/1998 | |
| WO | WO-00/76960 A1 | | 12/2000 | |
| WO | WO 2004/095929 | * | 11/2004 | A01N 43/00 |
| WO | WO-2005/122771 | | 12/2005 | |
| WO | WO 2005/122771 | | 12/2005 | |
| WO | WO 2007/031283 | | 3/2007 | |
| WO | WO-2007/031283 A2 | | 3/2007 | |
| WO | WO-2007/054471 | | 5/2007 | |

OTHER PUBLICATIONS

'Benalaxyl-Mdatasheet' (www.alanwood.net/pesticides/benalaxyl-m.html) (retrieved from the internet Mar. 19, 2010).*

* cited by examiner

FUNGICIDAL MIXTURES

The present invention relates to fungicidal mixtures comprising
(1) triticonazole of the formula I

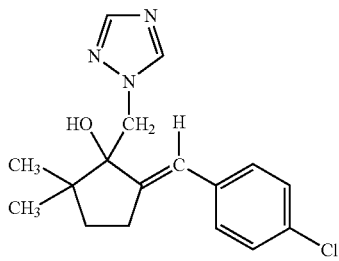

(I)

or salts or adducts thereof
and
(2) pyraclostrobin of the formula II

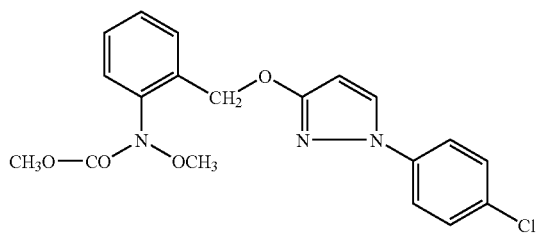

(II)

and
(3) at least one acylalanine selected from the group consisting of metalaxyl-M of the formula III

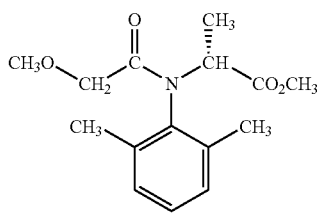

(III)

and
(4) kiralaxyl of the formula IV

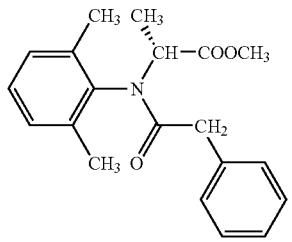

(IV)

in a synergistically effective amount.

Moreover, the invention relates to a method for controlling harmful fungi using mixtures of the compounds I to III, to the use of the compounds I to III for preparing such mixtures and to compositions comprising these mixtures.

Triticonazole of the formula I is described in EP-A 0 378 953.

Pyraclostrobin of the formula II is known from EP-A 0 804 421.

Metalaxyl-M of the formula III is described in WO 96/01559.

Kiralaxyl of the formula IV is known from WO 00/76960.

Moreover, mixtures of triticonazole of the formula I with other fungicides are known from WO 98/54969.

It is an object of the present invention, with a view to reducing the application rates and broadening the activity spectrum of the known compounds I to IV, to provide mixtures which, at a reduced total amount of active compounds applied, have improved activity against harmful fungi (synergistic mixtures).

We have found that this object is achieved by the mixture of triticonazole, pyraclostrobin and metalaxyl-M or kiralaxyl defined at the outset. Moreover, we have found that simultaneous, that is joint or separate, application of the compounds I to III or I, II and IV or successive application of the compounds I to III or I, II and IV allows better control of harmful fungi than is possible with the individual compounds.

Triticonazole of the formula I

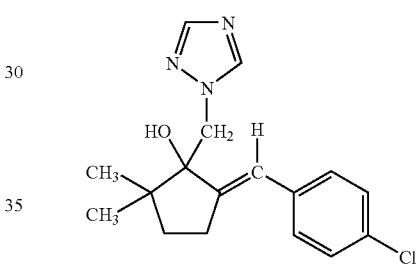

(I)

is described in EP-A 0 378 953.

Pyraclostrobin of the formula II

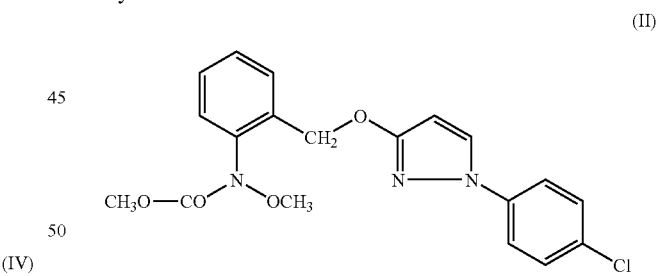

(II)

is described in EP-A 0 804 421.

Metalaxyl-M of the formula III

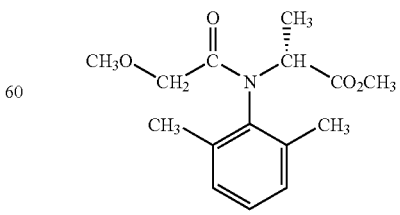

(III)

is described in WO 96/01559.

Kiralaxyl of the formula IV

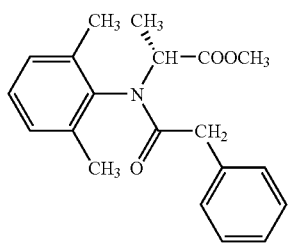

(IV)

is described in WO 00/76960.

Owing to the basic character of its nitrogen atoms, the compound I is capable of forming salts or adducts with inorganic or organic acids and with metal ions, respectively.

Examples of inorganic acids are hydrohalic acids, such as hydrogen fluoride, hydrogen chloride, hydrogen bromide and hydrogen iodide, sulfuric acid, phosphoric acid and nitric acid.

Suitable organic acids are, for example, formic acid, carbonic acid, and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid groups), where the alkyl or aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead and also of the elements of transition groups one to eight, in particular chromium, manganese, iron, cobalt, nickel, copper, zinc, and others. Particular preference is given to the metal ions of the elements of transition groups of the fourth period. The metals can be present in the various valencies that they can assume.

In many crops, dressing with fungicides delays or reduces emergence and results in a poorer establishment of the stand when the cultivation is started.

The mixtures of the compounds I to III or I, II and IV, or the simultaneous, that is joint or separate, use of one of the compounds I to IV, are/is distinguished in that these negative effects on the plants which, depending on the dosage, may also occur with triticonazole or pyraclostrobin, both when applied on their own and when applied as the 2-component mixture with III or IV, do not occur, or are not as pronounced. In addition, the mixtures have excellent activity against a broad spectrum of phytopathogenic fungi, in particular from the classes of the Ascomycetes, Basidiomycetes, Deuteromycetes and Peronosporomycetes (syn. Oomycetes). Some of them are systemically active and can be used in crop protection as foliar fungicides, as fungicides for seed dressing and as soil fungicides.

They are particularly important for controlling a multitude of fungi on various cultivated plants, such as bananas, cotton, vegetable species (for example cucumbers, beans, tomatoes and cucurbits), barley, grass, oats, coffee, potatoes, corn, fruit species, rice, rye, soybeans, grapevines, wheat, ornamental plants, sugar cane and also on a large number of seeds.

They are especially suitable for controlling the following plant diseases:

*Alternaria* species on vegetables, rapeseed, sugar beet and fruit and rice,

*Aphanomyces* species on sugar beet and vegetables,

*Bipolaris* and *Drechslera* species on corn, cereals, rice and lawns,

*Blumeria graminis* (powdery mildew) on cereals,

*Botrytis cinerea* (gray mold) on strawberries, vegetables, flowers and grapevines,

*Bremia lactucae* on lettuce,

*Cercospora* species on corn, soybeans, rice and sugar beet,

*Cochliobolus* species on corn, cereals, rice (e.g., *Cochliobolus sativus* on cereals, *Cochliobolus miyabeanus* on rice),

*Colletotricum* species on soybeans and cotton,

*Drechslera* species on cereals and corn,

*Exserohilum* species on corn,

*Erysiphe cichoracearum* and *Sphaerotheca fuliginea* on cucurbits,

*Fusarium* and *Verticillium* species on various plants,

*Gaeumanomyces graminis* on cereals,

*Gibberella* species on cereals and rice (e.g., *Gibberella fujikuroi* on rice), Grain staining complex on rice,

*Helminthosporium* species on corn and rice,

*Michrodochium nivale* on cereals,

*Mycosphaerella* species on cereals, bananas and peanuts,

*Phakopsara pachyrhizi* and *Phakopsara meibomiae* on soybeans,

*Phomopsis* species on soybeans and sunflowers,

*Phytophthora infestans* on potatoes and tomatoes,

*Plasmopara viticola* on grapevines,

*Podosphaera leucotricha* on apples,

*Pseudocercosporella herpotrichoides* on cereals,

*Pseudoperonospora* species on hops and cucurbits,

*Puccinia* species on cereals and corn,

*Pyrenophora* species on cereals,

*Pyricularia oryzae, Corticium sasakii, Sarocladium oryzae, S. attenuatum, Entyloma oryzae* on rice,

*Pyricularia grisea* on lawns and cereals,

*Pythium* spp. on lawns, rice, corn, cotton, rapeseed, sunflowers, sugar beet, vegetables and other plants,

*Rhizoctonia* species on cotton, rice, potatoes, lawns, corn, rapeseed, potatoes, sugar beet, vegetables and other plants,

*Sclerotinia* species on rapeseed and sunflowers,

*Septoria tritici* and *Stagonospora nodorum* on wheat,

*Erysiphe* (syn. *Uncinula*) *necator* on grapevines,

*Setospaeria* species on corn and lawns,

*Sphacelotheca reilinia* on corn,

*Thievaliopsis* species on soybeans and cotton,

*Tilletia* species on cereals,

*Ustilago* species on cereals, corn and sugar beet, and

*Venturia* species (scab) on apples and pears.

The mixtures according to the invention are also suitable for controlling harmful fungi such as *Paecilomyces variotii* in the protection of materials (for example wood, paper, paint dispersions, fibers or fabrics) and in the protection of stored products.

The compounds I to III or I, II and IV can be applied simultaneously, that is jointly or separately, or in succession, the sequence, in the case of separate application, generally not having any effect on the result of the control measures.

When preparing the mixtures, it is preferred to employ the pure active compounds I to III or I, II and IV, to which further active compounds against harmful fungi or against other pests, such as insects, arachnids or nematodes, or else herbicidal or growth-regulating active compounds or fertilizers can be added according to need.

Usually, mixtures of the compounds I to III or I, II and IV are employed. However, in certain cases mixtures of the compounds I to III or I, II and IV with, if appropriate, a plurality of active components may be advantageous, such as, for example, mixtures of the compounds I to III with the compound IV or further fungicides or mixtures of the compounds I, II and IV with further fungicides.

The mixing ratio (weight ratio) of the compounds I, II and III or IV is chosen such that a synergistic fungicidal action occurs, for example compound I:compound II:compound III or compound IV such as 100 to 1:100 to 1:100 to 1, in particular 10 to 1:10 to 1:10 to 1, for example 5 to 1:5 to 1:5 to 1, in particular 3 to 1:3 to 1:3 to 1, preferably 2 to 1:2 to 1:2 to 1. The mixing ratio includes, for example, the mixtures I:II:III or IV such as 100:1:1 to 1:100:1 to 1:1:100. The synergistic action of the mixture manifests itself in that the fungicidal action of the mixture I+II+III or IV is greater than the sum of the fungicidal actions of I and of II and of III or IV.

The further active components are, if desired, added in a ratio of from 20:1 to 1:20 to the compounds I to III or I, II and IV.

Depending on the type of compound and the desired effect, the application rates of the mixtures according to the invention are, especially in the case of areas under agricultural cultivation, from 5 g/ha to 2000 g/ha, preferably from 20 to 900 g/ha, in particular from 50 to 750 g/ha.

Correspondingly, the application rates for the compound I are generally from 1 to 1000 g/ha, preferably from 10 to 900 g/ha, in particular from 20 to 750 g/ha.

Correspondingly, the application rates for the active compound II are generally from 1 to 1000 g/ha, preferably from 10 to 900 g/ha, in particular from 40 to 750 g/ha.

Correspondingly, the application rates for the active compound III or IV are generally from 1 to 1000 g/ha, preferably from 10 to 900 g/ha, in particular from 40 to 750 g/ha.

In the treatment of seed, application rates of mixture are generally from 1 to 1000 g/100 kg of seed, preferably from 1 to 750 g/100 kg, in particular from 5 to 500 g/100 kg.

The method for controlling harmful fungi is carried out by the separate or joint application of the compounds I to III or I, II and IV or a mixture of the compounds I to III or I, II and IV by spraying or dusting the seeds, the plants or the soil before or after sowing of the plants or before or after emergence of the plants.

The mixtures according to the invention, or the compounds I to III or I, II and IV can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner, for example by extending the active compound with solvents and/or carriers, if desired using emulsifiers and dispersants. Solvents/auxiliaries suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

The following are examples of formulations:
1. Products for Dilution with Water
A) Water-Soluble Concentrates (SL)

10 parts by weight of a compound according to the invention are dissolved in 90 parts by weight of water or of a water-soluble solvent. As an alternative, wetting agents or other auxiliaries are added. The active compound dissolves upon dilution with water. This gives a formulation having an active compound content of 10% by weight.

B) Dispersible Concentrates (DC)

20 parts by weight of a compound according to the invention are dissolved in 70 parts by weight of cyclohexanone with addition of 10 parts by weight of dispersant, for example polyvinylpyrrolidone. Dilution with water gives a dispersion. The active compound content is 20% by weight.

C) Emulsifiable Concentrates (EC)

15 parts by weight of a compound according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D) Emulsions (EW, EO)

25 parts by weight of a compound according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (e.g. Ultraturrax) and made into a homogeneous emulsion. Dilution with water gives an emulsion. The formulation has an active compound content of 25% by weight.

E) Suspensions (SC, OD)

In an agitated ball mill, 20 parts by weight of a compound according to the invention are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.

F) Water-Dispersible Granules and Water-Soluble Granules (WG, SG)

50 parts by weight of a compound according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G) Water-Dispersible Powders and Water-Soluble Powders (WP, SP)

75 parts by weight of a compound according to the invention are ground in a rotor-stator mill with addition of 25 parts by weight of dispersants, wetting agents and silica gel. Dilution with water gives a stable dispersion or solution of the active compound. The active compound content of the formulation is 75% by weight.

2. Products to be Applied Undiluted

H) Dustable Powders (DP)

5 parts by weight of a compound according to the invention are ground finely and mixed intimately with 95 parts by weight of finely divided kaolin. This gives a dustable product having an active compound content of 5% by weight.

J) Granules (GR, FG, GG, MG)

0.5 part by weight of a compound according to the invention is ground finely and associated with 99.5 parts by weight of carriers. Current methods are extrusion, spray-drying or the fluidized bed. This gives granules to be applied undiluted having an active compound content of 0.5% by weight.

K) ULV Solutions (UL)

10 parts by weight of a compound according to the invention are dissolved in 90 parts by weight of an organic solvent, for example xylene. This gives a product to be applied undiluted having an active compound content of 10% by weight.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible thereby to apply formulations comprising over 95% by weight of active compound, or even to apply the active compound without additives.

Oils of various types, wetters, adjuvants may be added to the active compounds, even, if appropriate, not until immediately prior to use (tank mix). These agents are typically admixed with the compositions according to the invention in a weight ratio of from 1:100 to 100:1, preferably from 1:10 to 10:1.

The compounds I to III or I, II and IV or the mixtures or the corresponding formulations are applied by treating the harmful fungi, the plants, seeds, soils, areas, materials or spaces to be kept free from them with a fungicidally effective amount of the mixture or, in the case of separate application, with the compounds I to III or I, II and IV. Application can be carried out before or after infection by the harmful fungi.

The fungicidal effect of the individual compounds and the mixtures according to the invention was demonstrated by the following tests:

The active compounds were prepared separately or jointly as a stock solution with 25 mg of active compound which was made up to 10 ml using a mixture of acetone and/or DMSO and the emulsifier Uniperol® EL (wetting agent having emulsifying and dispersing action based on ethoxylated alkylphenols) in a volume ratio of solvent/emulsifier of 99 to 1. The mixture was then made up with water to 100 ml. This stock solution was diluted with the solvent/emulsifier/water mixture described to the concentration of active compounds stated below.

The visually determined percentages of infected leaf areas were converted into efficacies in % of the untreated control:

The efficacy (E) is calculated as follows using Abbot's formula:

$$E = (1 - \alpha/\beta) \cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of mixtures of active compounds were determined using Colby's formula (Colby, S. R. "Calculating synergistic and antagonistic responses of herbicide combinations", Weeds, 15, pp. 20-22, 1967) and compared with the observed efficacies.

Colby's formula:

$$E = x + y - x \cdot y / 100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b

USE EXAMPLE

Seed Treatment of Bentgrass

Seeds of bentgrass were seed-treated with the products and concentrations listed. Triticonazol and Pyraclstrobin were used as 200 g/l FS-formulation. Metalaxyl als a 17.7% LS-formulation.

Treated sees were planted at the day of treatment and then kept under humid conditions in the greenhouse. 7 days after plating the ground coverage by emerged plants were estimated in percentage.

| Treatment | Concentration | % covered ground |
|---|---|---|
| untreated | — | 10.8% |
| Triticonazol & Pyraclostrobin | 10 g a.i./100 kg seed & 10 g a.i./100 kg seed | 8.5% |
| Metalaxyl-M | 20 g a.i./100 kg seed | 36.3% |
| Triticonazol & Pyraclostrobin & Metalaxyl-M | 10 g a.i./100 kg seed & 10 g a.i./100 kg seed & 20 g a.i./100 kg seed | 39.5% |

The data show that the negative effect of the mixture of TTZ and Pyraclostrobin can be over compensated by Metalaxyl-M.

The invention claimed is:

1. A fungicidal mixture, comprising
(1) triticonazole of the formula I

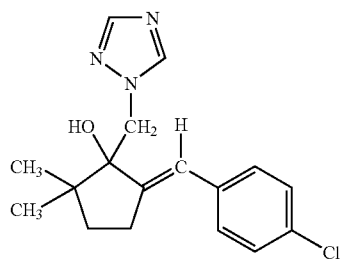

or salts or adducts with metal ions thereof; and (2) pyraclostrobin of the formula II

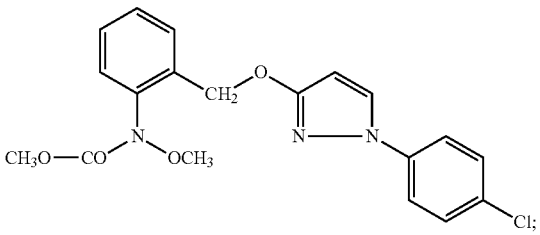

and (i)-metalaxyl-M of the formula III

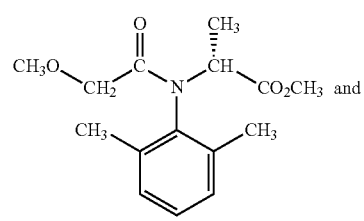

in a synergistically effective amount.

2. The fungicidal mixture according to claim 1, wherein the weight ratio of triticonazole of the formula I to pyraclostrobin of the formula II and metalaxyl-M of the formula III is from 100 to 1:100 to 1:100 to 1.

3. A fungicidal composition, comprising the fungicidal mixture according to claim 1 and a solid or liquid carrier.

4. Seed, comprising the mixture according to claim 1 in an amount of from 1 g to 1000 g per 100 kg of seed.

5. A method for controlling harmful fungi, which comprises treating the fungi, their habitat or the plants, seeds, soils, areas, materials or spaces to be kept free from them with the fungicidal mixture according to claim 1.

6. A method for controlling harmful fungi, which comprises treating the fungi, their habitat or the plants, seeds, soils, areas, materials or spaces to be kept free from them with the compounds of the formulae I to III (1) triticonazole of the formula I

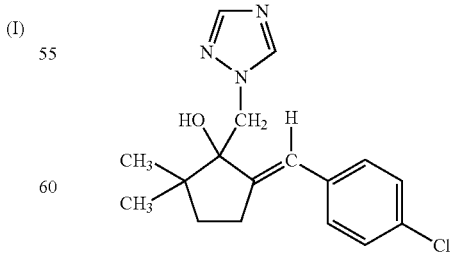

or salts or adducts with metal ions thereof; and (2) pyraclostrobin of the formula II

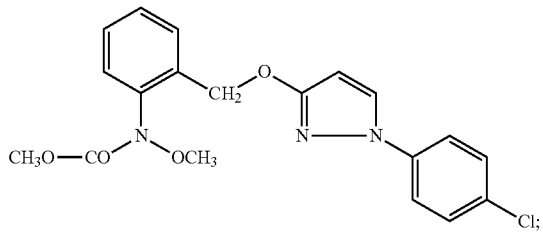

and (i)-metalaxyl-M of the formula III

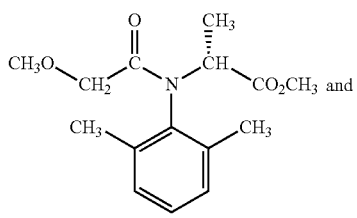

in a synergistically effective amount wherein the compounds are applied simultaneously, that is together or separately, or in succession.

7. The method according to claim 5, wherein the fungicidal mixture or the compounds of the formulae I to III comprising (1) triticonazole of the formula I

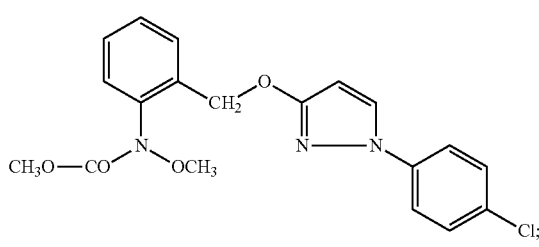

or salts or adducts with metal ions thereof; and (2) pyraclostrobin of the formula II

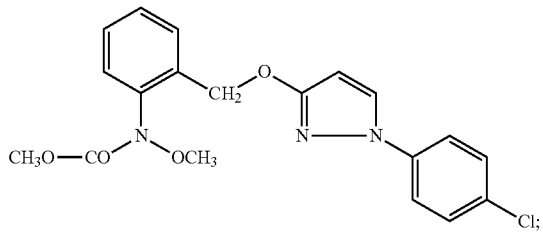

and (i)-metalaxyl-M of the formula III

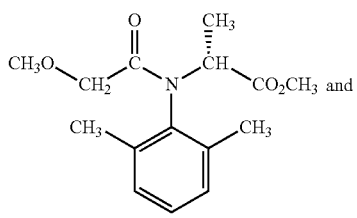

in a synergistically effective amount is/are applied in an amount of from 5 g/ha to 2000 g/ha.

8. The method according to claim 5, wherein the compounds I to III or the mixture comprising (1) triticonazole of the formula I

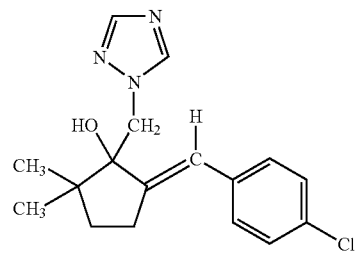

or salts or adducts with metal ions thereof; and (2) pyraclostrobin of the formula II

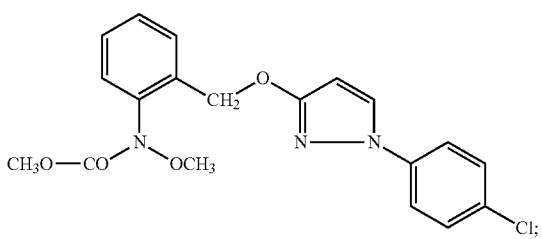

and (i)-metalaxyl-M of the formula III

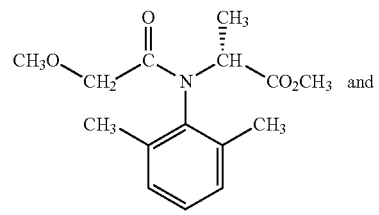

in a synergistically effective amount are/is applied in an amount of from 1 g to 1000 g per 100 kg of seed.

9. The method according to claim 6 wherein the fungicidal mixture or the compounds of the formulae I to III comprising (1) triticonazole of the formula I

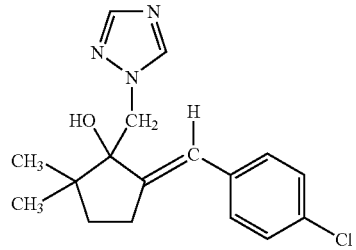

or salts or adducts with metal ions thereof;
and
(2) pyraclostrobin of the formula II

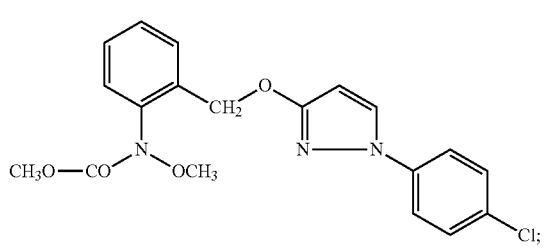

and (i)-metalaxyl-M of the formula III

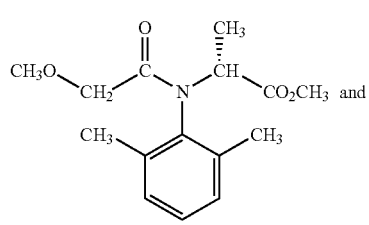

in a synergistically effective amount is/are applied in an amount of from 5 g/ha to 2000 g/ha.

10. The method according to claim 6 wherein the compounds I to III or the mixture (1) triticonazole of the formula I

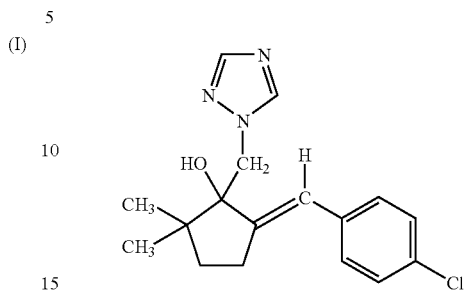

or salts or adducts with metal ions thereof;
and
(2) pyraclostrobin of the formula II

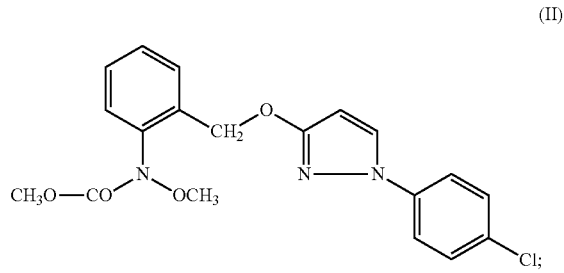

and (i)-metalaxyl-M of the formula III

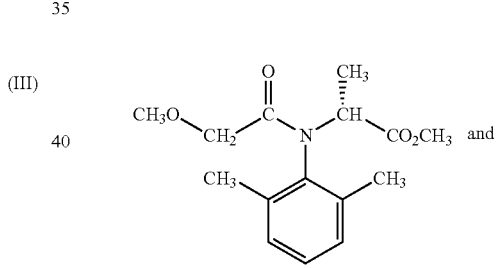

in a synergistically effective amount are/is applied in an amount of from 1 g to 1000 g per 100 kg of seed.

* * * * *